US00PP26801P3

(12) United States Plant Patent

Stewart et al.

(10) Patent No.: US PP26,801 P3

(45) Date of Patent: Jun. 7, 2016

(54) STRAWBERRY PLANT NAMED 'DRISSTRAWFORTYFOUR'

(50) Latin Name: *Fragaria×ananassa*
Varietal Denomination: DrisStrawFortyFour

(71) Applicant: DRISCOLL STRAWBERRY ASSOCIATES, INC., Watsonville, CA (US)

(72) Inventors: Philip J. Stewart, Watsonville, CA (US); Michael D. Ferguson, Moorpark, CA (US); Renae Robertson, Santa Maria, CA (US); Joanne F. Coss, Pebble Beach, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 90 days.

(21) Appl. No.: 14/121,763

(22) Filed: Oct. 15, 2014

(65) Prior Publication Data

US 2016/0113174 P1 Apr. 21, 2016

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Annette Para

(74) *Attorney, Agent, or Firm* — Jondle & Associates, P.C.

(57) ABSTRACT

A new and distinct variety of strawberry plant named 'DrisStrawFortyFour' particularly characterized by medium red strongly glossy fruit, early harvest maturity and moderate resistance to powdery mildew, is disclosed.

3 Drawing Sheets

Genus and species: *Fragaria×ananassa.*
Variety denomination: 'DrisStrawFortyFour'.

BACKGROUND OF THE NEW PLANT

The present invention relates to a new and distinct strawberry variety designated 'DrisStrawFortyFour' and botanically known as *Fragaria×ananassa.* This new strawberry variety was discovered in Monterey County, Calif. in October 2009 and originated from a cross between proprietary open pollinated bulk (unpatented) and the proprietary male parent '112N245' (unpatented). A single plant was selected and asexually propagated via tissue culture and vegetative cuttings in Shasta County, Calif.

'DrisStrawFortyFour' underwent further testing in Monterey County, Calif. for five years (2009-2014). The present invention has been found to retain its distinctive characteristics through successive asexual propagations via stolons and tissue culture.

Plant Breeder's Rights for this variety have not been applied for. 'DrisStrawFortyFour' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Monterey County, Calif.

1. Medium red, strongly glossy fruit;
2. Early harvest maturity; and
3. Moderate resistance to powdery mildew.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from nine-month-old plants.

DESCRIPTION OF THE NEW VARIETY

Figure 1:
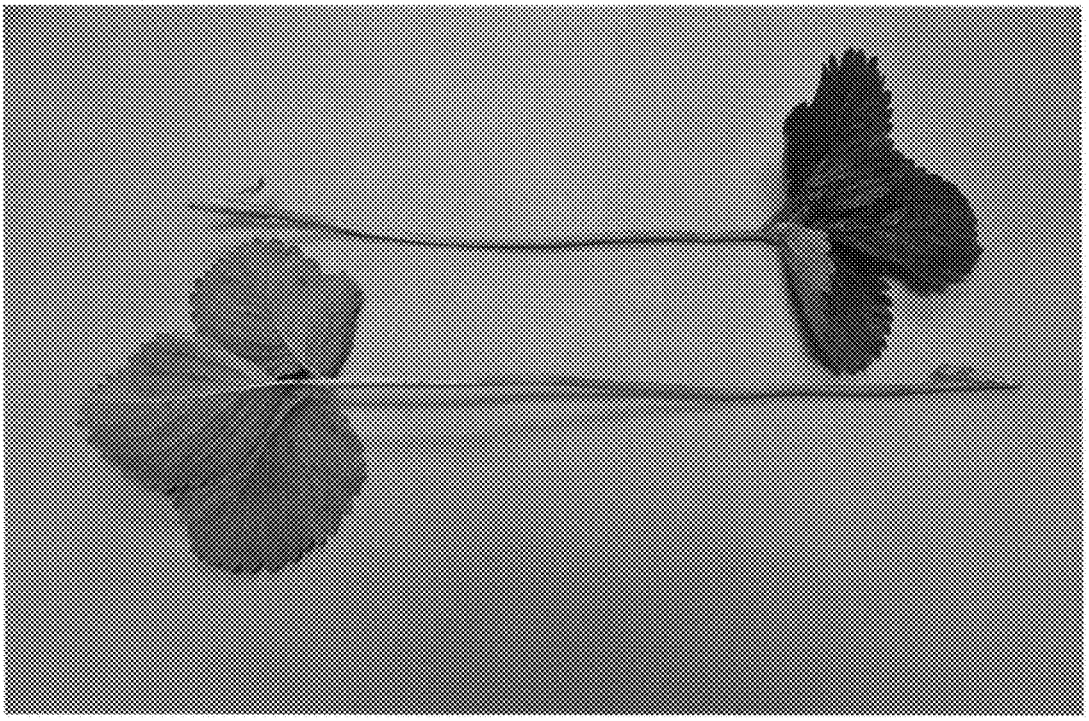
FIG. 1 shows upper and lower surfaces of the leaves of the plant with three leaflets.
Figure 2:
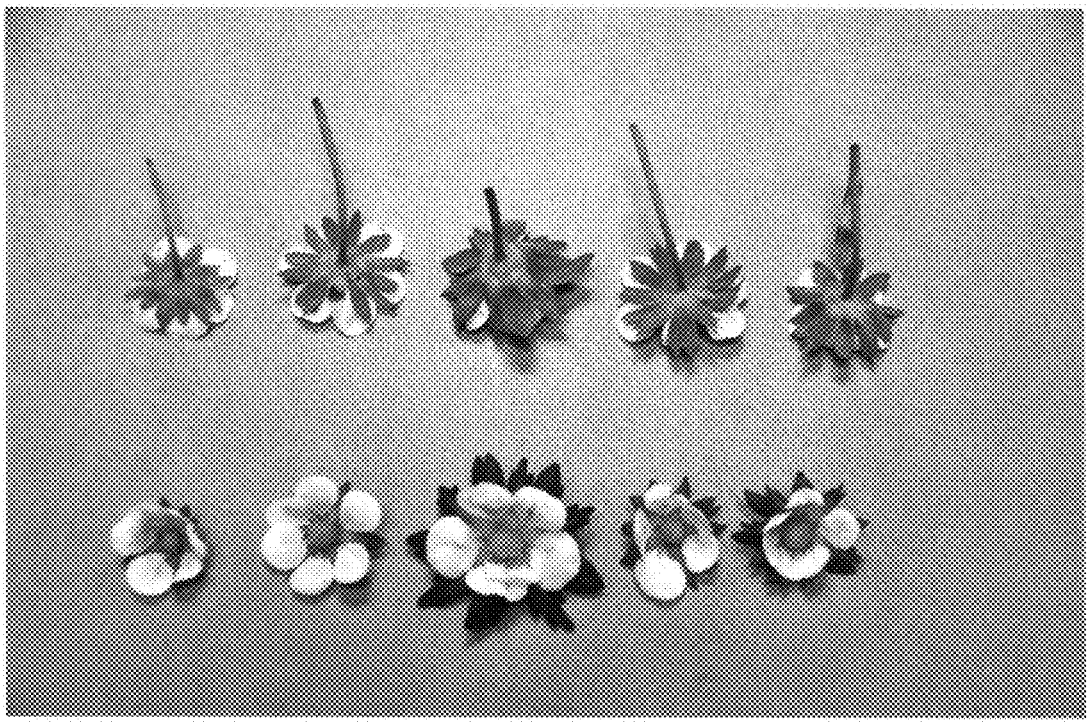
FIG. 2 shows both upper and lower surfaces of the flowers.
Figure 3:
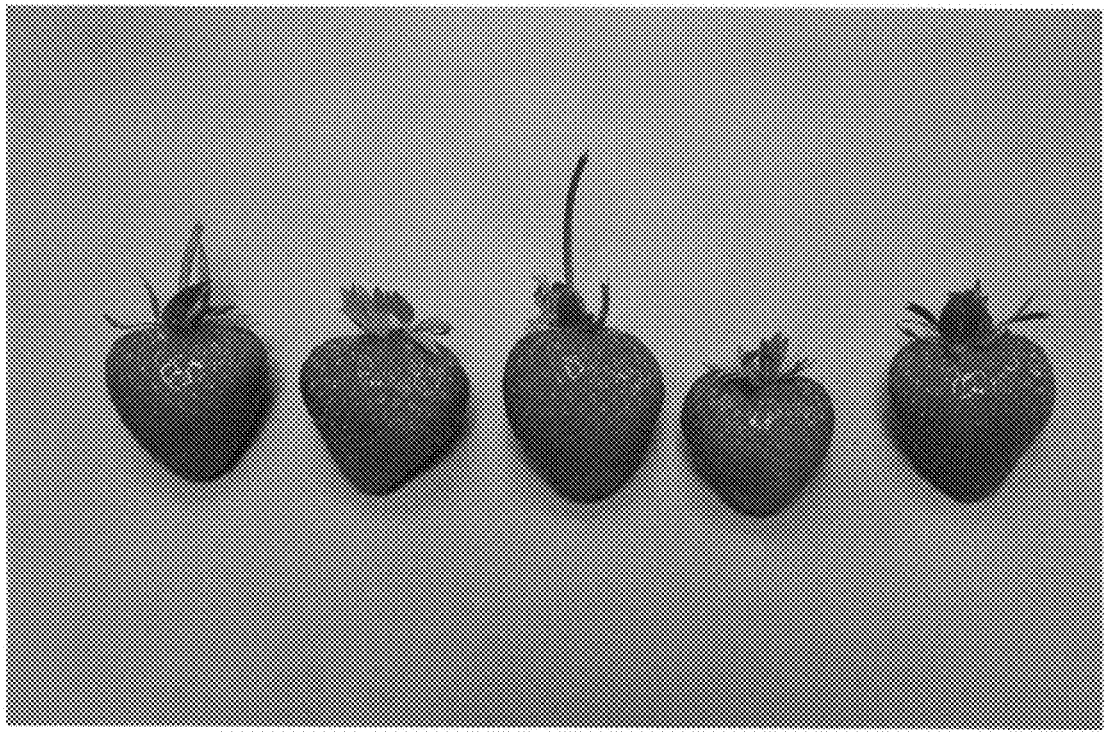
FIG. 3 shows the whole fruit.
Figure 4:
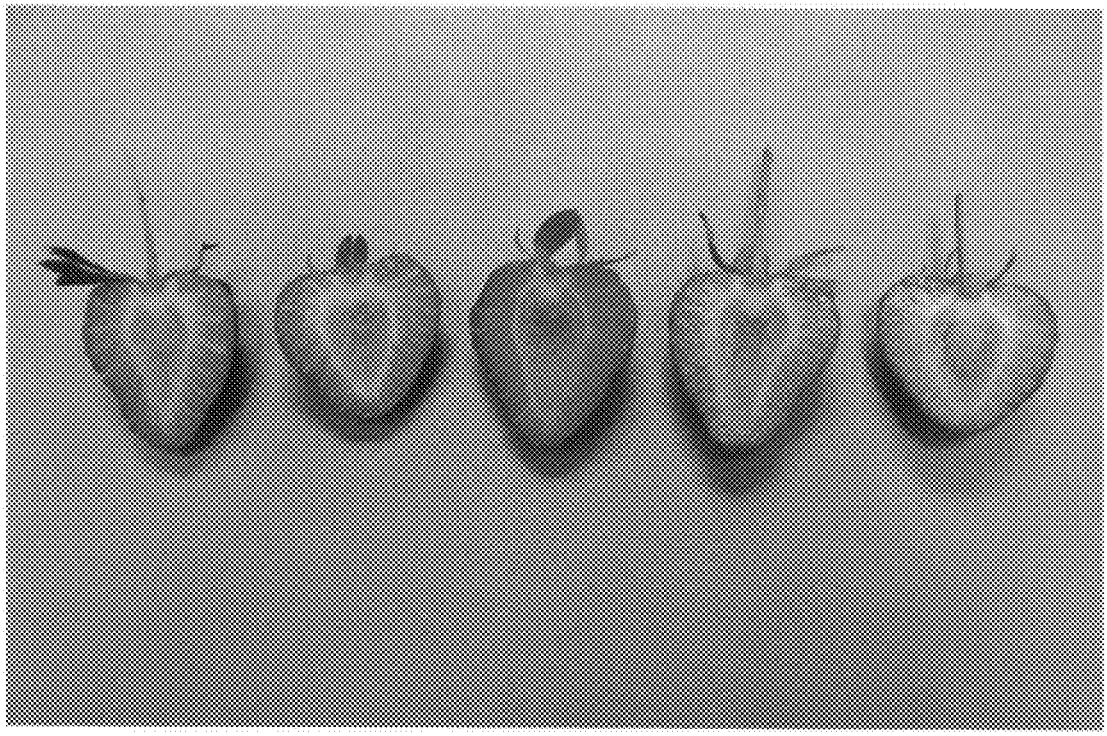
FIG. 4 shows the fruit in longitudinal cross-section.
Figure 5:
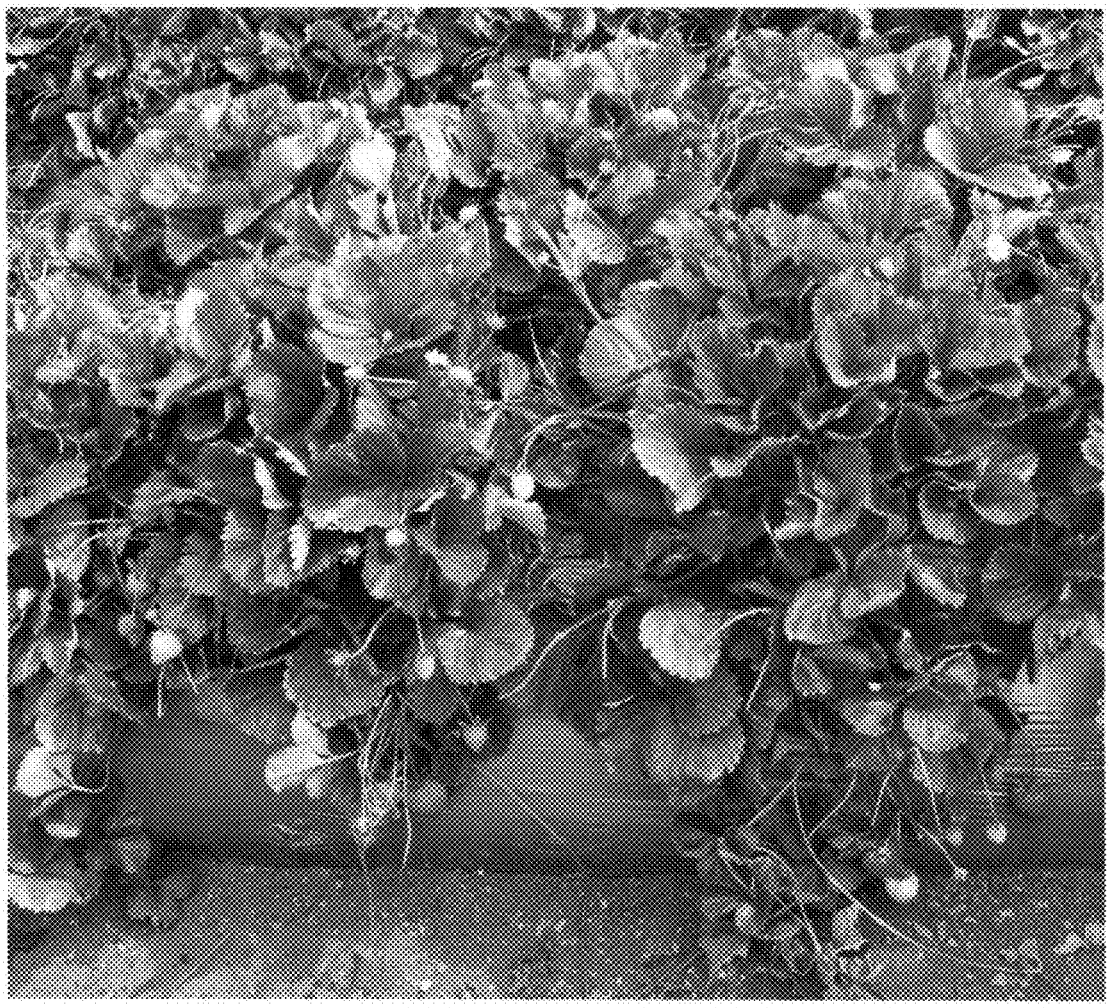
FIG. 5 shows the whole plant.

The following detailed descriptions set forth the distinctive characteristics of 'DrisStrawFortyFour'. The data which define these characteristics is based on observations taken in Monterey County, Calif. from 2009 to 2014. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortyFour' has not been observed under all possible environmental conditions. The botanical description of 'DrisStrawFortyFour' was taken from nine-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawFortyFour'.

Parentage:
- *Female parent.*—Proprietary open pollinated bulk (unpatented).
- *Male parent.*—The proprietary variety '112N245' (unpatented).

Plant:
- *Height.*—33.7 cm.
- *Diameter.*—58.2 cm.
- *Number of crowns/plant.*—6.
- *Habit.*—Globose — semi-upright.
- *Density of individual plant.*—Medium to dense.
- *Vigor* (*health and hardiness of plant*).—Very strong.

Terminal leaflets:
- *Size.*—Medium. Length: 8.0 cm. Width: 7.5 cm. Length/width ratio: 1.1 (As long as broad).
- *Number of teeth/terminal leaflet.*—25.
- *Shape of teeth.*—Rounded to crenate.
- *Color.*—Upper surface: RHS N137C (Medium green). Lower surface: RHS 138B (Medium green).
- *Shape in cross section.*—Slightly concave.
- *Blistering.*—Weak.
- *Glossiness.*—Medium.
- *Number of leaflets.*—More than three.
- *Shape.*—Orbicular.
- *Base shape.*—Rounded.
- *Apex descriptor.*—Rounded.
- *Margin.*—Crenate.
- *Margin profile.*—Revolute (margins rolled backwards).
- *Variegation.*—Absent.

Petiole:
- *Length.*—Medium; 22.0 cm.
- *Diameter.*—3.86 mm.
- *Pubescence.*—Dense.
- *Pose of hairs.*—Outwards — horizontal.
- *Color.*—RHS 144A (Medium yellow-green).
- *Bract frequency.*—0.

Petiolule:
- *Length.*—12.72 mm.
- *Diameter.*—2.04 mm.
- *Color.*—RHS 144B (Medium yellow-green).

Stipule:
- *Length.*—31.7 mm.
- *Width.*—8.45 mm.
- *Pubescence.*—Very dense.
- *Stipule anthocyanin coloration.*—Strong to very strong; RHS 50C (Light red).

Inflorescence:
- *Position relative to foliage.*—Above.
- *Number of flowers per plant.*—18 (Medium).
- *Time of flowering* (*50% of plants at first flower*).—Early.
- *Flowering interval.*—February-November.
- *Flower size.*—Medium.
- *Flower diameter.*—13.98 mm.
- *Petals.*—Shape: Orbicular. Apex: Rounded. Base: Concavo-convex. Margin: Entire. Spacing: Free. Length: 10.51 mm. Width: 9.51 mm. Length/width ratio: 1.1 (As long as broad). Petal number per flower: 6. Color (upper surface): RHS NN155C (White).
- *Calyx.*—Diameter: 17.52 mm. Diameter relative to corolla: Same size. Inner calyx diameter relative to outer: Same size. Insertion of calyx: Level. Pose of calyx segments: Reflexed — upwards. Size of calyx in relation to fruit: Same size. Adherence of calyx: Very strong.
- *Sepal.*—Shape: Elliptical. Apex: Convex. Margin: Entire. Length: 6.72 mm. Width: 4.32 mm. Sepal number: 12.
- *Receptacle color.*—RHS 154B (Light yellow-green).
- *Stamen.*—Present. Anther color: RHS 17C (Medium yellow-orange).
- *Pedicel.*—Attitude of hairs: Outwards — horizontal.

Fruiting truss:
- *Length.*—Long; 23.4 cm.
- *Diameter at base of truss.*—3.54 mm.
- *Number of berries per fruiting truss.*—4.
- *Attitude at first picking.*—Prostrate.
- *Color at base of truss.*—RHS 144B (Medium yellow-green).

Fruit:
- *Relative fruit size.*—Small.
- *Length.*—39.44 mm.
- *Width.*—38.03 mm.
- *Length/width ratio.*—1.0 (As long as broad).
- *Fruit hollow length.*—19.38 mm.
- *Fruit hollow width.*—21.19 mm.
- *Fruit hollow length/width ratio.*—0.9 (As long as broad).
- *Fruit hollow center* (*cavity*).—Small.
- *Fruit weight.*—24.3 g.
- *Predominant fruit shape.*—Conical.
- *Difference in shape between primary and secondary fruits.*—Slight.
- *Evenness of fruit surface.*—Even or very slightly uneven.
- *Fruit skin color.*—RHS 45B (Medium red).
- *Evenness of fruit color.*—Even or very slightly uneven.
- *Fruit glossiness.*—Strong.
- *Achenes.*—Insertion of achenes: Level with surface. Coloration (sunward side of berry): RHS 184B (Medium greyed-purple). Coloration (shaded side of berry): RHS 152D (Medium yellow-green). Number per berry: 146. Weight (weight of achenes divided by total # seed): 0.00834 g. Width of band without achenes: Narrow.
- *Firmness of flesh* (*when fully ripe*).—Firm.
- *Color of flesh* (*excluding core*).—RHS 40C (Light red).
- *Color of core.*—RHS 40D (Light red).
- *Evenness of flesh color.*—Even.
- *Distribution of flesh color.*—Marginal and central.
- *Sweetness.*—Weak.
- *Acidity.*—Medium.
- *Texture when tasted.*—Medium.
- *Type of bearing.*—Day neutral.
- *Harvest interval.*—May-early November
- *Harvest maturity.*—Early.
- *Production.*—2434.0 grams per plant.

Disease and pest resistance:
- *Botrytis fruit rot.*—Moderately susceptible.
- *Powdery mildew.*—Moderately resistant.
- *Lygus herperus* (*Lygus bug*): Moderately susceptible.

COMPARISON WITH PARENTAL AND COMMERCIAL VARIETIES

When 'DrisStrawFortyFour' is compared to the open pollinated bulk (unpatented), the open pollinated bulk was a group of uncharacterized seedlings that generally had less regular fruit shape, lighter fruit color and lighter leaf color than 'DrisStrawFortyFour'.

When 'DrisStrawFortyFour' is compared to the male parent '112N245' (unpatented), 'DrisStrawFortyFour' is a more vigorous and upright plant with higher yields and lighter colored fruit than '112N245'. In addition, 'DrisStrawFortyFour' produces more runners in the field than '112N245'.

When 'DrisStrawFortyFour' is compared to the commercial variety 'Monterey' (U.S. Plant Pat. No. 19,767), 'DrisStrawFortyFour' has a slightly concave leaf shape in cross section, dense petiole pubescence and petals with a concavo-convex base shape, whereas 'Monterey' has a mostly concave leaf shape in cross section, moderate to heavy petiole pubescence and petals with an attenuate base shape.

When 'DrisStrawFortyFour' is compared to the commercial variety 'DrisStrawThirtyOne' (U.S. Plant Pat. No. 24,317), 'DrisStrawFortyFour' has an average of six crowns per plant and a globose—semi-upright growth habit, whereas 'DrisStrawThirtyOne' has an average of three crowns per plant and an upright growth habit. Additionally, 'DrisStrawFortyFour' has fruit with strong glossiness and medium acidity, whereas 'DrisStrawThirtyOne' has fruit with medium glossiness and weak acidity.

We claim:

1. A new and distinct variety of strawberry plant named 'DrisStrawFortyFour', substantially as illustrated and described herein.

* * * * *